(12) United States Patent
Ball

(10) Patent No.: US 6,858,717 B1
(45) Date of Patent: Feb. 22, 2005

(54) METHOD FOR OBTAINING MODIFIED POLYSACCHARIDES

(75) Inventor: Steven Ball, Bourghelles (FR)

(73) Assignee: Biogemma, Paris (FR)

( * ) Notice: Subject to any disclaimer, the term of this patent is extended or adjusted under 35 U.S.C. 154(b) by 0 days.

(21) Appl. No.: 09/719,978

(22) PCT Filed: Jun. 16, 1999

(86) PCT No.: PCT/FR99/01446

§ 371 (c)(1),
(2), (4) Date: Apr. 25, 2001

(87) PCT Pub. No.: WO99/66056

PCT Pub. Date: Dec. 23, 1999

(30) Foreign Application Priority Data

Jun. 16, 1998 (FR) .......................................... 98 07589

(51) Int. Cl.[7] .......................... A01H 5/00; C12N 15/31; C12N 15/52; C12N 15/54; C12N 15/82
(52) U.S. Cl. .................. 536/23.2; 536/23.7; 435/320.1; 800/284; 800/317.2; 800/320.1; 800/320.2; 800/320.3
(58) Field of Search ...................... 356/23.7; 435/320.1, 435/419, 468; 800/317.2, 320.1, 320.2, 320.3, 278, 284, 288; 536/23.1, 23.2

(56) References Cited

FOREIGN PATENT DOCUMENTS

| WO | WO 96/27674 | | 9/1996 |
| WO | WO 97/22703 | * | 6/1997 |

OTHER PUBLICATIONS

Visser R. et al., Towards modifying plants for altered starch content and composition. TIBTECH 1993; vol. 11, pp. 63–68.*

Shewmaker C. et al., Modifying Starch Biosynthesis with Transgenes in Potatoes. Plant Physiology 1992; vol. 100; pp. 1083–1086.*

Stark D et al., Increased Starch and Dry Matter Deposition in Transgenic Russet Burbank Potato Tubers. Poster Abstract #714.*

Kobmann et al. Transgenic plants as a tool to understand starch biosynthesis, 1995. Carbohydrate Bioengineering pp. 271–278.*

Willmitzer et al. Starch Synthesis in Transgenic Plants, 1993 pp. 33–39.* by A. Buleon et al., "Starches from A to C$^1$", *Plant Physiology*, vol. 115, No. 3, Nov. 1997, pp. 949–957.

by B. Fuchs et al., "Disproportionating Transglycosylase (D–Enzyme) in Green Algae and Cyanobacteria: Partial Purification and Characterization", *Zeitschrift Fuer Natuforschung Section C Biosciences*, vol. 49, No. 3–4, 1994, pp. 163–170.

* cited by examiner

*Primary Examiner*—David T. Fox
*Assistant Examiner*—Russell Kallis
(74) *Attorney, Agent, or Firm*—Young & Thompson

(57) ABSTRACT

The invention concerns a method for obtaining plants producing modified polysaccharides (such as starch or glycogen), said modified polysaccharides extracted from said plants and the products prepared from said modified polysaccharides. The invention also concerns a method for obtaining modified starch or modified glycogen which consists in contacting a starch or a glycogen with an α-1,4 glucanotransferase enzyme.

7 Claims, 5 Drawing Sheets

□ 2,5 mg/ml amylopectine
○ 1 mg/ml amylopectine
△ 0,25 mg/ml amylopectine

METHOD FOR OBTAINING MODIFIED POLYSACCHARIDES

The present invention relates to a method for obtaining plants which produce modified polysaccharides (such as starch or glycogen), to these modified polysaccharides extracted from these plants, and to the products prepared from these modified polysaccharides.

Starch is the energetic storage polyoside in plants. It constitutes the main calorific intake of the animal and human diet, and is also a major source of plant raw material for nondietary uses. Starch is composed of two distinct polysaccharide fractions: amylose and amylopectin. Amylose, which represents the minor fraction of starch, consists of glucose residues joined together via α-1,4 linkages and exhibits less than 1% branching. Amylopectin, which represents the major fraction of starch, consists of glucose residues joined together via α-1,4 linkages and exhibits approximately 5% branching, which consists of glucose residues linked to the principal polymer via an α-1,6 linkage. The asymmetric distribution of the branching of amylopectin is responsible for the unlimited growth of the molecules and, consequently, of grains of starch, and also accounts for most of the physicochemical properties of starch.

The biosynthesis of starch depends on a pathway, the main biochemical steps of which are the synthesis of ADP-glucose, followed by the transfer of this precursor to the α-1,4 position on a glucan by (ADP-glucose: 1,4-α-D-glucan 4-α-D-glucosyl)transferases, the polymer formed being branched by the action of so-called branching enzymes: 1,4-α-D-glucan 6-α-D-(1,4-α-D-glucano)-transferases. Appended FIG. 1 is a simplified scheme of the metabolism of starch so far known to those skilled in the art.

Known plant α-1,4 glucanotransferases (or 4-α-D-glucanotransferases) are commonly referred to as "D enzymes", for "disproportionating enzymes" They catalyze the transfer of glucan from one 1,4-α-glucan molecule to another (intermolecular transglycosylation). The rules of action of the D enzyme on oligosaccharide substrates are represented schematically as follows:

Scheme: Example of disproportionating activity by the D enzyme on maltotriose amylopectin, the molecular weight of the debranched amylopectin and the number and length of the α-1,6 branchings. Takaha et al. have concluded from this that the D enzyme does not have a direct role concerning the structures and amounts of starch produced, but plays a role in the growth of the plant and its development, the amylopectin and amylose being used as donor molecules for the transfer of maltooligosaccharide to glucose, thus allowing the breaking up and solubilization of starch grains (Takada et al., 1998).

Surprisingly, the authors of the present invention have discovered that α-1,4 glucanotransferases, and in particular D enzymes, are in fact involved in the biosynthesis of starch by transferring oligosaccharides to an amylopectin precursor. These enzymes can, in particular, transfer oligosaccharides originating from the pool of oligosaccharides produced in vivo by debranching of the amylopectin precursor during amylopectin maturation. They can in particular transfer oligosaccharides which may contain, for example, from 2 to 20, in particular from 2 to 6, glucose residues. Appended FIG. 2 shows the role of the D enzyme in the starch metabolism cycle, as discovered by the authors of the present invention.

This discovery has been exploited in order to modify, as a function of the level of active α-1,4 glucanotransferase enzyme present, the length distribution for the chains of amylopectin, which is present in particular in the storage organs of plants. The invention also applies to glycogen, which is present in a smaller amount than amylopectin in plants, but which can be found, for example, in sweetcorn seeds, allowing, in the same way, the modification of the length distribution for the chains of glycogen.

A subject of the present invention is, therefore, the use of a nucleic acid encoding an α-1,4 glucanotransferase enzyme or a sequence which is the antisense sequence to said sequence encoding an α-1,4 glucanotransferase enzyme, for modifying the length distribution for the external chains of starch (i.e. of amylopectin and/or of amylose) or of glycogen.

A subject of the present invention is more particularly a method for modifying the length distribution for the chains of the amylopectin of a starch, or for the chains of a glycogen, in which the activity of an α-1,4 glucanotransferase enzyme is increased or decreased in the cells of a plant such that said plant produces a modified starch which

| Acceptor (n) | Donor (x) | ⇆ Product (n + 2) | + Donor −2 |
| --- | --- | --- | --- |
| *G~G~G$_{OH}$ | + *G~G~G$_{OH}$ | ⇆ *G~G~G~G~G$_{OH}$ | + *G$_{OH}$ |
| *G~G~G~G~G$_{OH}$ | + *G~G~G$_{OH}$ | ⇆ *G~G~G~G~G~G~G$_{OH}$ | + *G$_{OH}$ |
| *G~G~G$_{OH}$ | + *G~G~G~G~G~G$_{OH}$ | ⇆ *G~G~G~G~G$_{OH}$ | + *G~G~G~G~G$_{OH}$ |
| *G~G~G~G~G$_{OH}$ | + *G~G~G~G~G$_{OH}$ | ⇆ *G~G~G~G~G~G~G$_{OH}$ | + *G~G~G$_{OH}$ |

Maltose cannot be used as a donor substrate, and only a linkage at the end of the maltotriose can be attacked. In addition, the first linkage on the nonreducing side and the penultimate linkage on the reducing side are resistant to the action of the enzyme.

Takaha et al. have reported, at the AAB (Association of Applied Biologists) Congress which was held from 6 to 8 Apr. 1998, in Edinburgh, UK (congress on the subject: "Production and use of starch"), that potatoes with no D enzyme grow more slowly than control potatoes and that, despite this, the content of starch present in the tubers, and its composition, appear to be normal with regard, in particular, to the appearance of the starch grains by optical or electron microscopy, the proportions of amylose and differs from the starch produced naturally by the plants, by the length distribution for the chains of the amylopectin, or produces a modified glycogen which differs from the glycogen produced naturally, by the length distribution for its external chains.

According to a first embodiment of the invention, the level of expression of endogenous α-1,4 glucanotransferase enzyme is decreased so as to cause the production of a starch comprising an amylopectin which is enriched in chains containing less than 6 glucose residues, with respect to a starch produced naturally. The decrease in the expression of an endogenous α-1,4 glucanotransferase enzyme can be in particular produced according to the method comprising the steps consisting in:

a) constructing an expression vector comprising an antisense nucleotide sequence of the gene encoding said endogenous α-1,4 glucanotransferase enzyme;

b) transforming a plant cell with said expression vector;

c) regenerating the plant from the cell transformed in step b, said transgenic plant thus obtained producing a starch comprising an amylopectin in which the chain length distribution is modified, in particular in the sense of an enrichment in chains containing less than 6 glucose residues.

Advantageously, said plant cell transformed according to step b) is also transformed with antisense nucleotide sequences of the genes encoding enzymes which affect the distribution of the length of the oligosaccharides produced in the metabolism of starch, such as phosphorylases and amylases.

Another possibility for decreasing the activity of the α-1,4 glucanotransferase enzyme in plant cells is to express ribozymes, which are RNA molecules which act as enzymes which catalyze specifically the cleavage of transcripts encoding the α-1,4 glucanotransferase enzyme, by techniques known to those skilled in the art (EP 321 021).

It is also possible to obtain a plant having a modification of the expression of α-1,4 glucanotransferase enzyme, by the so-called "transwitch" method described in WO 90/12084.

The activity of the endogenous α-1,4 glucanotransferase enzyme can also be decreased by mutagenesis of the plant cells, either by U.V. irradiation or with a chemical mutagenic agent, or by insertion of transposons. The transposable elements have the capacity to disturb the expression of genes into which they are inserted, and to generate deletions, rearrangements and mutations at the target locus (McClintock et al., 1950).

One transposon mutagenesis technique which can be advantageously used is Mutator transposon mutagenesis confirmed by reverse genetic screening (Bensen et al., 1995) (Das et al., 1995). This technique implements the steps consisting in crossing a "Mutator" line with hybrids of the plants of interest, and then screening the F1 plants obtained by PCR with a primer specific for the transposons and a primer specific for the nucleotide sequence encoding the α-1,4 glucanotransferase enzyme. The F2 seeds obtained from the F1 screened plants make it possible to produce plants the phenotype of which is then analyzed.

According to a second embodiment of the invention, the level of expression of α-1,4 glucanotransferase enzyme in the plant is increased so as to cause the production of a starch comprising an amylopectin which is enriched in chains containing at least 9 glucose residues, with respect to a starch produced naturally, said α-1,4 glucanotransferase enzyme being identical to the endogenous α-1,4 glucanotransferase enzyme or being of heterologous origin.

The increase in the level of α-1,4 glucanotransferase enzyme can in particular be produced according to the method comprising the steps consisting in:

a) constructing an expression vector comprising a nucleotide sequence encoding an α-1,4 glucanotransferase enzyme, which can be an α-1,4 glucanotransferase enzyme identical to the endogenous α-1,4 glucanotransferase enzyme, or which can be of heterologous origin;

b) transforming a plant cell with said expression vector;

c) regenerating the plant from the cell transformed in step b), said transgenic plant thus obtained producing a starch comprising an amylopectin in which the chain length distribution is modified, in particular in the sense of an enrichment in chains containing at least 9 glucose residues.

Advantageously, said plant cell transformed according to step b) is also transformed with nucleotide sequences encoding enzymes which affect the distribution of the length of the oligosaccharides produced in the metabolism of starch, such as phosphorylases and amylases. Preferably, the α-1,4 glucanotransferase enzyme targeted is a D enzyme.

Said nucleotide sequence encoding an α-1,4 glucanotransferase enzyme can be of heterologous origin. It can thus correspond in particular to an enzyme chosen from the D enzyme of potato (Takaha et al., 1993) or the D enzyme of *Chlamydomonas reinhardtii*.

Also included in the invention is a nucleic acid comprising a nucleotide sequence chosen from the sequence SEQ ID No. 1, a homologous sequence and a fragment of this sequence encoding a protein having α-1,4 glucanotransferase enzymatic activity.

The invention also comprises the sequences complementary to the sequence SEQ ID No. 1, or to its homologues and fragment, which can be used as antisense sequences in the method of the invention.

The sequence SEQ ID No. 1 represents a fragment of genomic DNA of the gene encoding the D enzyme of *Chlamydomonas reinhardtii*.

The expression "homologous nucleotide sequence" is intended to mean any nucleotide sequence which differs from the sequence SEQ ID No. 1 by substitution, deletion and/or insertion of a nucleotide or of a small number of nucleotides, at positions such that these homologous nucleotide sequences encode homologous polypeptides as defined hereinafter.

Preferably, such a homologous nucleotide sequence is at least 75% identical to the sequence SEQ ID No. 1, preferably at least 85%, more preferably at least 95*.

Preferentially, such a homologous nucleotide sequence hybridizes specifically to the sequence complementary to the sequence SEQ ID No. 1, under stringent conditions. The parameters which define the stringency conditions depend on the temperature at which 50% of the paired strands separate from each other (Tm).

For sequences comprising more than 30 bases, Tm is defined by the equation: Tm=81.5+0.41(% G+C)+16.6Log (concentration of cations)−0.63(*formamide)−(600/number of bases) (Sambrook et al., Molecular Cloning, A laboratory manual, Cold Spring Harbor laboratory Press, 1989, pages 9.54–9.62).

For sequences less than 30 bases long, Tm is defined by the equation: Tm=4(G+C)+2(A+T).

Under suitable stringency conditions, at which aspecific sequences do not hybridize, the hybridization temperature is approximately from 5 to 30° C., preferably from 5 to 10° C. below Tm, and the hybridization buffers used are preferably solutions of high ionic strength, such as a 6×SSC solution, for example.

The term "nucleotide fragment" is intended to mean any fragment of the sequence SEQ ID No. 1, or of the nucleotide sequences homologous to the sequence SEQ ID No. 1, which encodes a peptide or a protein having α-1,4 glucanotransferase enzymatic activity, as defined above.

A subject of the present invention is also a cloning and/or expression vector comprising a nucleotide sequence as defined above.

The construction of an abovementioned expression vector is within the scope of those skilled in the art, A according to standard techniques. Said expression vector can contain an antisense nucleotide sequence of the gene encoding said endogenous α-1,4 glucanotransferase enzyme, according to the first embodiment of the invention, or a nucleotide sequence encoding an α-1,4 glucanotransferase enzyme, according to the second embodiment of the invention. The nucleotide sequence encoding an α-1,4 glucanotransferase enzyme is associated with elements which allow its expression in the plant, namely in particular a promoter and a transcription terminator.

The transformation of plant cells can be carried out by transferring the abovementioned vectors into protoplasts, in particular after incubation of the latter in a solution of polyethylene glycol in the presence of divalent cations ($Ca^{2+}$).

The transformation of plant cells can also be carried out by electroporation, in particular according to the method described in the article by Fromm et al., 1986.

The transformation of the plant cells can also be carried out using a gene gun which allows the projection, at very high speed, of metal particles coated with the DNA sequences of interest, thus delivering genes inside the cell nucleus, in particular according to the technique described in the article by Sanford (1988).

Another method for transforming the plant cells is that of cytoplasmic or nuclear microinjection.

According to a particularly preferred embodiment of the method of the invention, the plant cells are transformed by biolistics, i.e. by projection, by means of a particle gun, of microparticles coated with the nucleotide sequences to be transferred (J. Finner, 1992).

According to another embodiment of the method of the invention, the plant cells are transformed with a vector according to the invention, said cellular host being capable of infecting said plant cells by allowing the integration, into the genome of the latter, of the DNA sequences of interest initially contained in the genome of the abovementioned vector.

Advantageously, the abovementioned cellular host used is *Agrobacterium tumefaciens*, in particular according to the method described in the article by An et al., 1986, or *Agrobacterium rhizogenes*, in particular according to the method described in the article by Jouanin et al., 1987.

Preferentially, the transformation of the plant cells is carried out by transferring the T region of the tumour-inducing extrachromosomal circular plasmid Ti of *Agrobacterium tumefaciens*, using a binary system (Watson et al.).

In order to do this, two vectors are constructed. In one of these vectors, the T-DNA region was removed by deletion, with the exception of the right and left edges, a marker gene being inserted between them so as to allow the selection in the plant cells. The other partner of the binary system is an auxiliary plasmid Ti, this being a modified plasmid which has no more T-DNA but still contains the virulence genes vir required for the transformation of the plant cell. This plasmid is maintained in Agrobacterium.

Among the transcription terminators which can be used, mention may be made of the $^{35}$S polyA terminator of the cauliflower mosaic virus (CaMV), described in the article by Franck et al., (1980), or the NOS polyA terminator, which corresponds to the 3' noncoding region of the nopaline synthase gene of the plasmid Ti of the nopaline *Agrobacterium tumefaciens* strain (Depicker et al., 1982).

Among the transcription promoters which can be used, mention may be made in particular of:

the 35S promoter, or advantageously the double 35S constitutive promoter (pd35S) of CaMV, described in the article by Kay et al., 1987;

the PCRU promoter of the cruciferin gene of radish, allowing the expression of the associated sequences only in the seeds (or grains) of the transgenic plant obtained;

the PGEA1 and PGEA6 promoters, corresponding to the 5' noncoding region of the seed storage protein genes GEA1 and GEA6, respectively, of *Arabidopsis thaliana* (Gaubier et al., 1993), and allowing specific expression in the seeds;

the super-promoter PSP chimeric promoter (Ni M et al., 1995), consisting of the fusion of a triple repeat of a transcription-activating element of the promoter of the octopine synthase gene of *Agrobacterium tumefaciens*, of a transcription-activating element of the promoter of the mannopine synthase gene and of the mannopine synthase promoter of *Agrobacterium tumefaciens*;

the rice actin promoter followed by the rice actin intron (PRA-RIA) contained in the plasmid pActl-F4 described by Mc Elroy et al., 1991;

the HMGW (High Molecular weight Glutenin) promoter of barley;

the promoter of the yzein gene of maize (Pyzein), contained in the plasmid pγ63 and allowing expression in the albumen of maize seeds.

Among the plant cells capable of being transformed in accordance with the present invention, mention may be made of those of potato, of wheat, of maize and of rice.

A subject of the present invention is also a plant, or part of a plant, such as in particular potato, wheat, maize or rice, which produces a modified starch which differs from the starch produced naturally by the plants, by the length distribution for its external chains, or which produces modified glycogen which differs from the glycogen produced naturally, by the length distribution for its external chains, said plant or part of a plant being obtained by the method of the invention as described above.

The expression "part of a plant" is intended to mean in particular the storage organs naturally rich in starch, such as the seeds or tubers, or the organs naturally rich in glycogen, for example sweetcorn seeds. The expression "part of a plant" is also intended to mean the cells of said plant.

The invention also relates to a method for obtaining modified starch or modified glycogen, in which a starch or a glycogen is brought into contact with an α-1,4 glucanotransferase enzyme.

A subject of the present invention is more particularly a method for obtaining modified starch which differs from the starch produced naturally by the plants, by the length distribution for its external chains, in which:

the modified starch is extracted from the plants, or parts of plants, obtained according to the method of the invention as described above.

or a starch, extracted from plants, or parts of plants, and then solubilized, beforehand, is brought into contact with an α-1,4 glucanotransferase enzyme, in the presence of optionally modified polysaccharides or oligosaccharides.

The extraction of this starch is carried out according to standard techniques known to those skilled in the art. The solubilization of the starch is also known to those skilled in the art, and can be carried out by soaking and fractionation of the starch grain (Whistler et al., (1967)), or, for example, by heating. Alternatively, enzymes which break up starch, such as amylases, can be used.

According to one embodiment of the invention, said solubilized starch is brought into contact with an α-1,4 glucanotransferase enzyme, such as a D enzyme, in the presence of saccharides. Said saccharides can be, in particular, oligosaccharides which are chemically modified so as to modify the properties of the starch, for example its digestibility.

Advantageously, enzymes which affect the distribution of the length of the oligosaccharides produced in the metabolism of starch, such as phosphorylases and amylases, can be added to the α-1,4 glucanotransferase enzyme.

A subject of the present invention is also a method for obtaining modified glycogen which differs from the glycogen produced naturally (by plants or by an animal organism), by the length distribution for its external chains, in which:

the modified glycogen is extracted from the plants, or parts of plants, obtained according to the method of the invention as described above.

or a glycogen (of plant or animal origin) is brought into contact with an α-1,4 glucanotransferase enzyme, in the presence of optionally modified polysaccharides or oligosaccharides.

Said α-1,4 glucanotransferase enzyme, such as a D enzyme, brought into contact with the starch or glycogen, can originate from the same species of plant as that from which the starch is extracted, or can have a heterologous origin. The D enzyme can in particular be chosen from the D enzyme of potato (Takaha. et al., 1993) or the 62 kD D enzyme of *Chlamydomonas reinhardtii* as defined hereinafter. Advantageously, the D enzyme used is heat stable.

The D enzyme of *Chlamydomonas reinhardtii* is purified by the method comprising the steps consisting in:

centrifuging the *Chlamydomonas reinhardtii* strain;

precipitating the acellular fraction with protamine sulphate;

passing the supernatant obtained in the previous step through anion exchange chromatography;

subjecting the fraction not retained in the previous step to differential precipitation with ammonium sulphate;

subjecting the supernatant obtained in the previous step to molecular sieve chromatography;

concentrating the pellet obtained in the previous step, by cation exchange chromatography.

The purified D enzyme of *Chlamydomonas reinhardtii* thus obtained has a molecular weight of 62 kD. More generally, as a protein having α-1,4 glucanotransferase enzymatic activity, it is possible to use a protein or a peptide encoded by a nucleic acid comprising a nucleotide sequence chosen from the sequence SEQ ID No. 1, a homologous sequence or a fragment of this sequence.

A subject of the present invention is also the modified starch which differs from the starch produced naturally by the plants, by the length distribution for its chains, said modified starch being obtained by the method of the invention. In particular, the modified starch obtained by extracting and solubilizing the starch of plants, or parts of plants, and then bringing said solubilized starch into contact with an α-1,4 glucanotransferase enzyme, optionally in the presence of saccharides, contains an amylopectin in which the length distribution for the external chains is modified with respect to a starch produced naturally.

A subject of the present invention is also the modified glycogen which differs from the glycogen produced naturally (for example by the plants, but also glycogen of animal origin), by the length distribution for its chains, said modified glycogen being obtained by the method of the invention.

The starch modified in accordance with the present invention can be used directly or hydrolyzed in order to produce oligosaccharides of interest (in particular glucose). The production of starch modified in accordance with the invention may make it possible to decrease the amounts of enzymes required for such a hydrolysis.

Moreover, the starch modified in accordance with the invention can be used in the manufacture of diverse foodstuffs, in particular as an additive which increases the viscosity or promotes the formation of a gel.

The starch modified in accordance with the invention can also be used in many industries: paper and board industry, adhesives industry, textile industry, pharmaceutical industry (for the formulation of medicines), etc.

The starch modified in accordance with the invention can also undergo other modifications, in particular chemical modifications such as acid treatment, oxidation, esterification, etc., before its use.

A subject of the present invention is also the use of this modified starch or of this modified glycogen for preparing derived products, in particular food products.

A subject of the present invention is also the products thus prepared comprising modified starch which differs from the starch produced naturally by the plants, by the length of its external chains, or modified glycogen which differs from the glycogen produced naturally, by the length of its external chains.

The figures and examples hereinafter illustrate the invention without limiting the scope thereof.

LEGENDS OF THE FIGURES

FIG. 1 represents a simplified scheme of the metabolism of starch so far known to those skilled in the art.

All the steps described are compartmentalized in the plast.

①. Phosphoglucomutase

②. ADP-glucose pyrophosphorylase

③. Soluble and bound starch synthetases

④. Branching enzymes

⑤. Phosphorylase

⑥. Amylases, debranching enzymes, maltases

⑦. Hexokinase

Glc=glucose; Pi=inorganic phosphate

FIG. 2 represents a simplified scheme of amylopectin synthesis, in which the role of the D enzyme is demonstrated.

All the steps described are compartmentalized in the plast:

①. Conversion of G-6-P to G-1P by plastidial phosphoglucomutase

②. Synthesis of the glycosylnucleotide precursor ADP-glucose by ADP-glucose pyrophosphorylase (AGPase)

③. Elongation by soluble starch synthetases (SSs)°

④. Branching by branching enzymes (BEs)

⑤. Debranching by isoamylase (DBE) and release of oligosaccharides (MOS)

⑥. Reinsertion of the oligosaccharides produced by debranching, by the D enzyme.

WSP=water-soluble polysaccharides; MOS= maltooligosaccharides; G-6-P=glucose-6-phosphate; Glc= glucose.

The energetic cost of splicing by the DBE and the D enzyme described in this invention is 2 ATPs per glucan cleaved and reintroduced into the amylopectin in ⑥ (WSP$^{III}$). This cost ensues from the reactivation of the glucose produced by the D enzyme into ADP-glucose. The dotted line drawn from WSP$^{III}$ illustrates the possibility for the polysaccharide to be re-used as a substrate for elongation as long as the structure required for it to become insoluble in the grain has not been attained. The entry and exit from the cycle are illustrated by the arrows in bold lines, and consist, firstly, of ADP-glucose being synthesized and, secondly, of the polysaccharide being crystallized and becoming insoluble at the surface of the grain.

The synthesis of amylose occurs after the polysaccharide has become insoluble and takes place exclusively in the granule.

EXAMPLES

Figure 1:
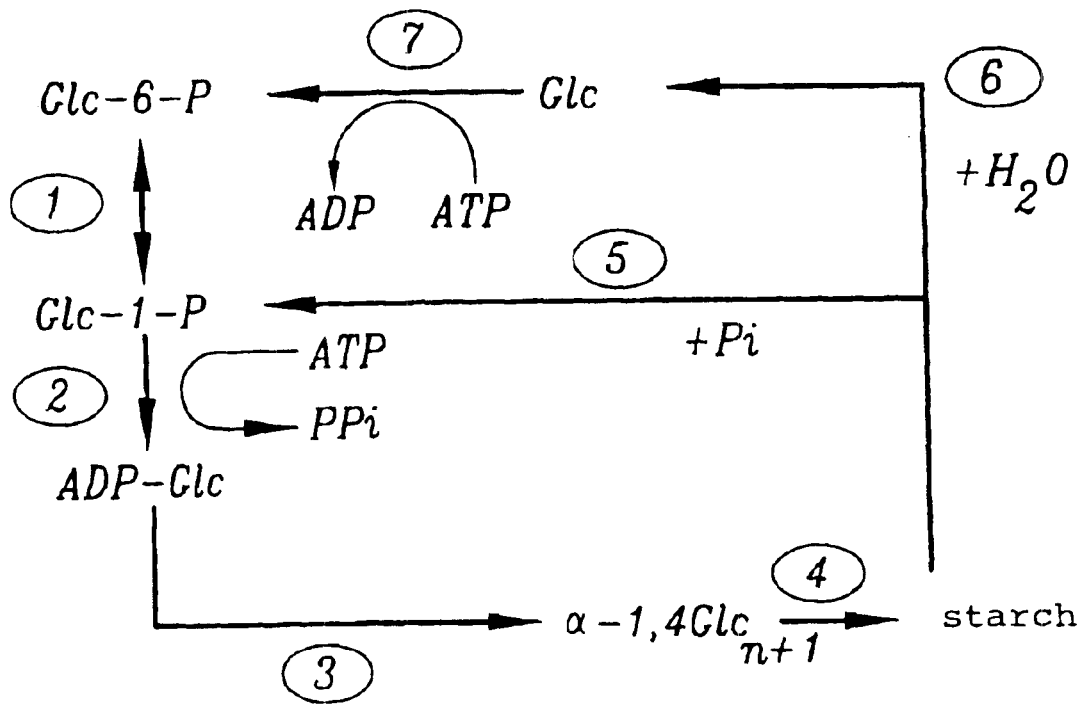
Figure 2:
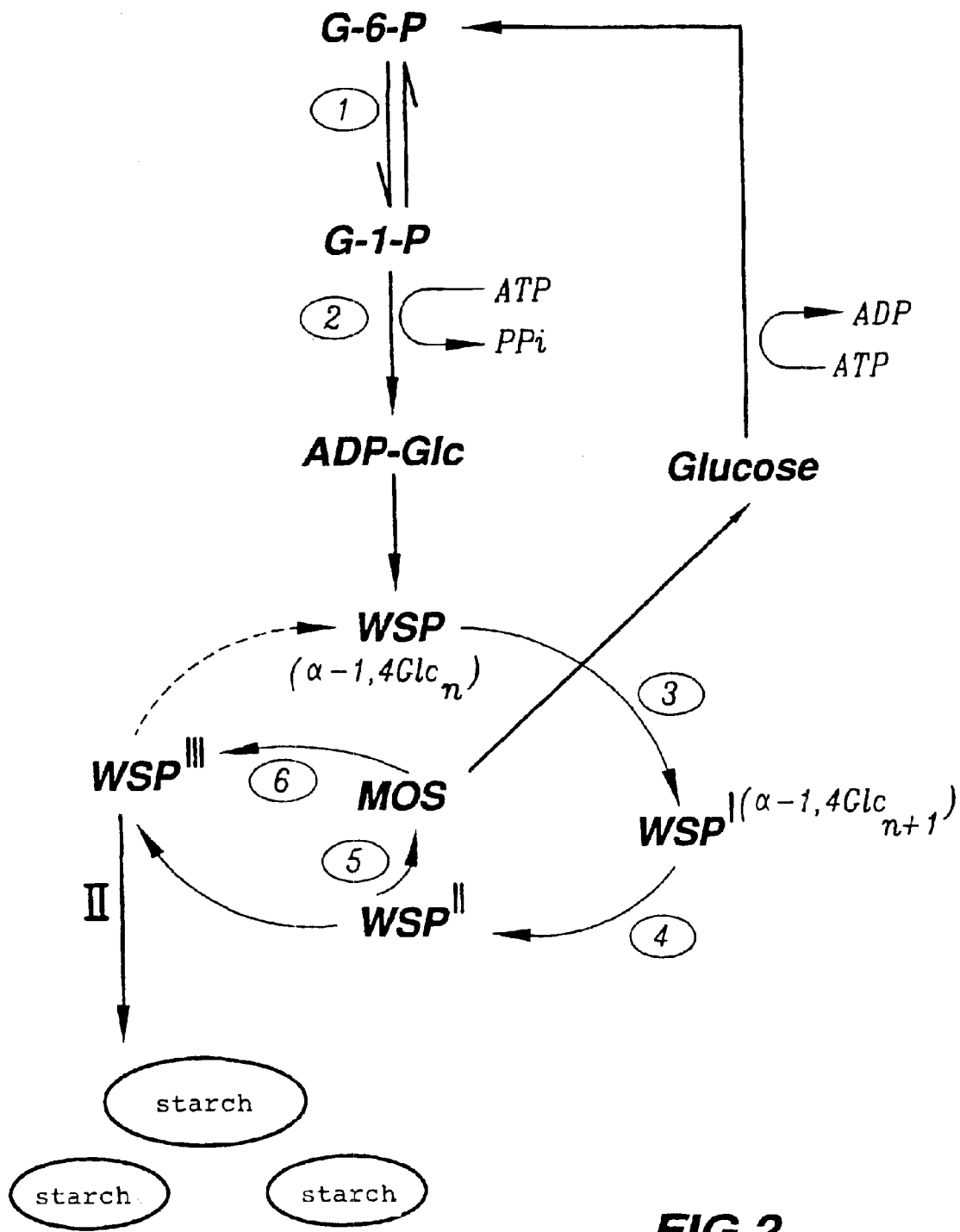

The authors of the present invention have studied the biosynthesis of starch using a suitable model: the alga *Chlamydomonas reinhardtii* (Buléon et al., 1997). Specifically, this unicellular organism stores a starch which is identical to that stored in the albumen of cereals, and also contains the same enzymes for biosynthesis of starch.

The authors of the present invention have selected a novel mutant of the alga *Chlamydomonas reinhardtii* which accumulates small linear oligosaccharides and has a rate of starch synthesis decreased by 90% (Example 1).

The residual starch comprises a novel modified structure characterized by an enrichment in amylose and by an amylopectin, the ultrashort (approximately 2, 3 or 4 glucose residues) chains of which are overabundant in relation to the chains of mean length (approximately from 9 to 18 glucose residues) (Examples 2 and 3).

The authors of the present invention have also shown that this mutant lacked a 62 kD protein normally present in the wild-type strains of *Chlamydomonas reinhardtii*, have identified this protein as being a 4-α-D-glucanotransferase (D enzyme) and have demonstrated novel functions of this D enzyme with respect to polysaccharides (Example 4).

These results can be exploited in order to obtain transgenic plants which produce modified polysaccharides (starch, glycogen) (Example 5).

The authors of the present invention have also demonstrated the role of the D enzyme in the degradation of maltooligosaccharides by phosphorylase (Example 6).

The authors of the present invention have, moreover, succeeded in cloning the sequences encoding the D enzyme of *Chlamydomonas reinhardtii* (Example 7).

They have finally shown that the expression of the mutation may vary as a function of the physiological conditions (Example 8).

EXAMPLE 1

Isolation of the Mutant sta11 of *Chlamydomonas reinhardtii*

Selection of the strain JV45J of *Chlamydomonas reinhardtii*.

During UV mutagenesis (12% survival) carried out on the wild-type reference strain 137° C. of *Chlamydomonas reinhardtii*, $5 \times 10^4$ plaques of cells, lacking nitrogen, were screened using an iodine pulverization method (Delrue et al., 1992). All the strains containing less than 20% of the normal amount of starch accumulated by the strain 137° C. are detected by their yellow colouration, and were characterized. A sample of five wild-type strains and seven mutants is inoculated, as plaques of cells, on a medium lacking nitrogen. The plaques were pulverized twice after five days of incubation in continuous bright light. The yellow plaques contain less than 12% of the amount of starch accumulated by the black plaques. The olive-green colour observed in certain relatively colourless plaques suggests the existence of a residual starch enriched in amylose. Selected from these strains were those which displayed transcomplementation with mutants carrying sta-1, sta6-1: ARG7, sta7-1::ARG7, sta5-1, which are defective for the loci encoding the large and small subunit of AGPase (STA1 and STAG), the 88 kDa isoamylase (STA7), or plastidial phosphoglucomutase (STA5). Only one strain from the $5 \times 10^4$ colonies (JV45J) showing a 90 to 95% reduction in the amount of starch synthesized under accumulation conditions (lack of nitrogen) was retained after this selection. This mutant was then crossed with a wild-type strain, and 257 products of meiosis were classified, respectively, into 119 strains of mutant phenotype for 128 clones of wild-type appearance.

A novel type of mutant (JV45J), which accumulates 4% of the normal amount of starch, could thus be isolated. In view of the segregation after crossing, the character responsible for the defective phenotype behaves as a Mendelian recessive character, and defines a novel genetic locus, named STA11, since the mutation transcomplements and recombines with all of the defects tested.

EXAMPLE 2

Characterization of the Polysaccharides of the Mutant sta11

Figure 3A:
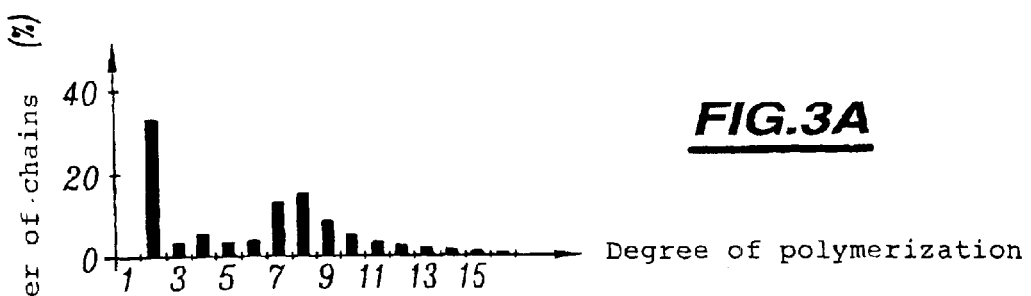
FIG. 3A represents the distribution of the lengths of the soluble non-debranched oligosaccharides accumulated by the mutant strain JV45J of *Chlamydomonas reinhardtii*.

The polysaccharides present in the strains carrying STA11 were isolated. In addition to the granular starch, the sta11-1 mutants accumulate an equivalent amount (5%) of soluble glucans, maltooligosaccharides of small size (FIG. 3A).

The simultaneous presence of a fraction of oligosaccharides and of the "low-starch" phenotype was found in all the strains carrying the mutation sta11-1 (n=50). The residual structure of the granular starch was measured by various techniques, including wide-angle X-ray diffraction analysis, transmission electron microscopy (TEM) and scanning electron microscopy (SEM), separation of the amylose and the amylopectin by gel filtration chromatography, NMR (Nuclear Magnetic Resonance) of the proton and enzymatic debranching on the amylose and the amylopectin thus purified.

1. The Granular Starch

The granular starch and the soluble glucans were analysed separately. The starch dispersed in aqueous DMSO and delipidized by precipitation with four volumes of ethanol was resuspended in 10 mM NaOH in order to then be fractionated by molecular sieve chromatography on CL2B sepharose gel.

a) Amylose and Amylopectin Composition (Gel Filtration).

The separation of the amylopectin and of the amylose is carried out by gel filtration of the mutant strain JV45J and the wild-type reference 137° C. The starch dissolved in 10 mM NaOH was fractionated by molecular sieve chromatography according to the method described by Delrue et al. (1992). A sample of each fraction was stained with iodine and the complete spectrum of the polysaccharide-iodine complex was recorded. Assays with amyloglucosidase revealed the presence of 30% of amylose (15% for the wild-type reference). In relation to the wild-type strain, the amylopectin is characterized by a $\lambda_{max}$ of the polysaccharide-iodine complex which has increased by 20 to 30 nm (from 550 to 570–580 nm). This latter characteristic is found in a large number of starches enriched in amylose.

Figure 5:
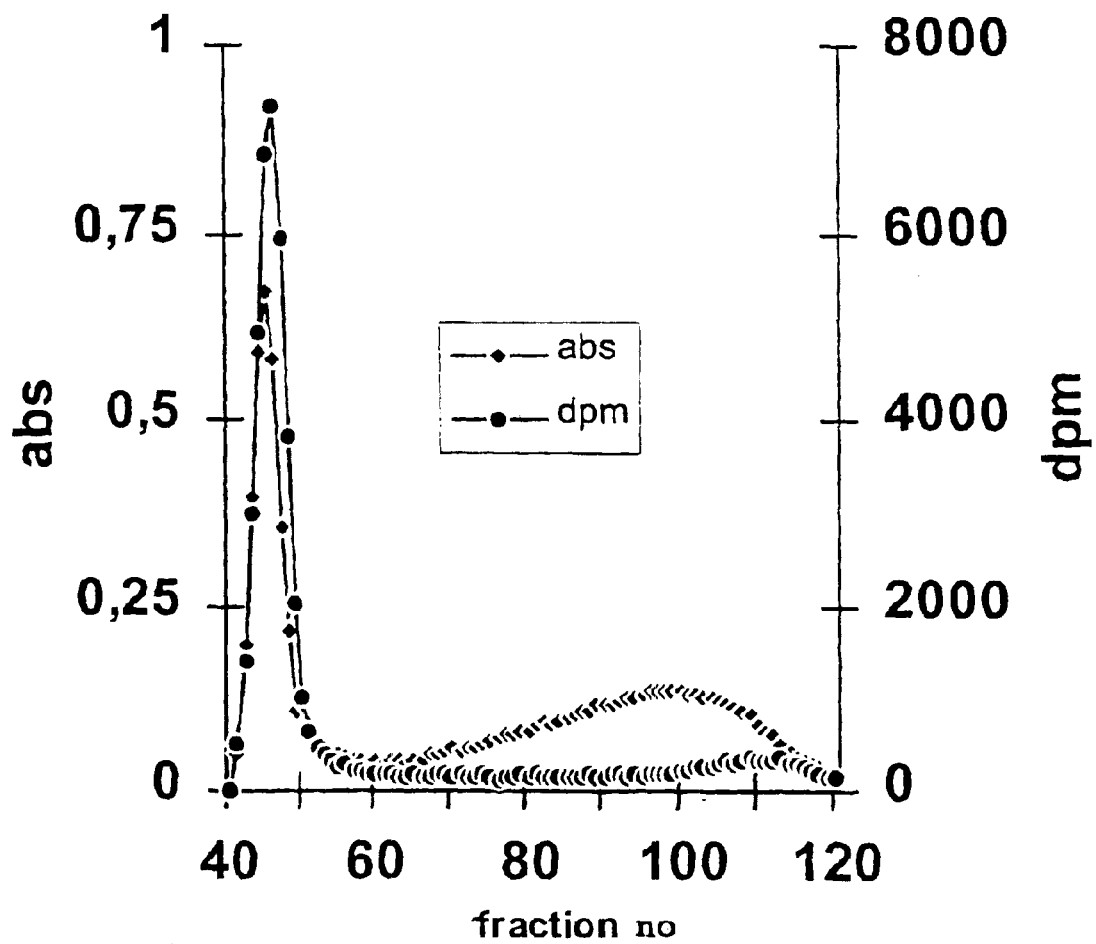
FIG. 5 represents the separation of the amylopectin and of the amylose of the starches of *JVV45J (sta11-1) and of 137° C. (wt) on CL-2B gel filtration chromatography. The mutant JV45J is represented by the radiolabelled starch (DPM) and the strain 137° C. is represented by the absorbance.

The gel filtration profiles described show a doubling of the amount of amylose in the mutant with respect to the wild-type, and an apparent modification of the distribution of chain lengths of the amylose fraction. A new segregation analysis of the amylopectin and of the amylose on CL-2B gel filtration chromatography was carried out using 500 μg of starch from JV45J (sta11-1) labelled with $^{14}$C and 10 mg of starch from 137° C. The results (FIG. 5) tend to confirm the data of the cosegregation study, namely a decrease in the length of the chains of amylose produced by the strain JV45J; the amylose appears, therefore, to be more abundant and lower in mass.

A radioactive count and the absorbence are determined for each fraction. The elution of the column is carried out in 10 mM sodium hydroxide.

b) Shape of the Granules and Crystalline Structure

The X-ray diffractograms show a change in the crystalline network from the wild-type A of high crystallinity towards a mixture of types A and B of much lower crystallinities. The shape of the granules is particularly modified and their overall size is reduced. In fact, the wild-type strain overall has grains with a smooth surface, whereas the mutant has grains of much smaller size with a rough and irregular grain surface.

2. The Soluble Glucans: Maltoolicoaaccharide of Small Size

The fraction of soluble glucans (WSP) was subjected to triple extraction with methanol chloroform. The aqueous phase was lyophilized and the dry pellet redissolved in a buffer and fractionated by molecular sieve chromatography eon a TSK-HW-50 column as has been described by Mouille et al., 1996. Unlike the soluble fractions (WSP) purified from isoamylase-deficient mutants, no phytoglycogen or other soluble polysaccharide of considerable mass was found. On the other hand, the WSP fraction accumulated by the sta11 mutants consists exclusively of relatively unbranched (less than 1.5% branching) oligosaccharides of low mass (FIG. 3A).

EXAMPLE 3

Demonstration of a Modification of the Amylopectin

Enzymatic Debranching with Isoamylase and Examination of the Chain Length Distribution:

The amylose and amylopectin fractions obtained by molecular sieve chromatography then underwent enzymatic debranching with isoamylase, followed by electrophoretic separation of the debranched chains. The results illustrated in FIG. 3 establish the novelty of the structure exhibited by the amylopectin of the strain JV45J. Specifically, the amylopectin exhibits an increase in chains conventionally absent from the structure.

Figure 3B:
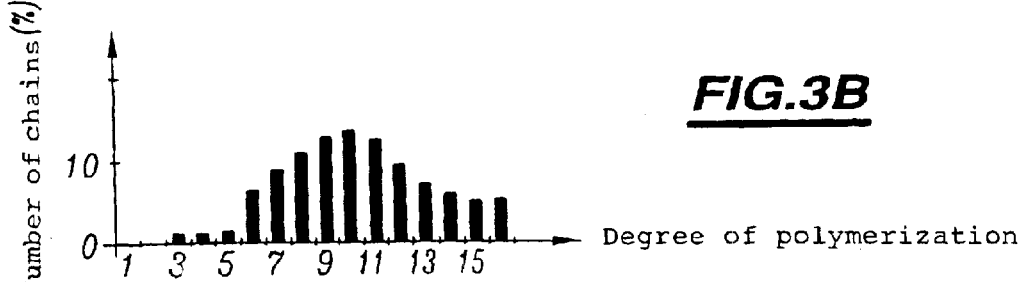
FIG. 3B represents the length distribution for the chains of the debranched amylopectin of the wild-type *Chlamydomonas reinhardtii* strain.
Figure 3C:
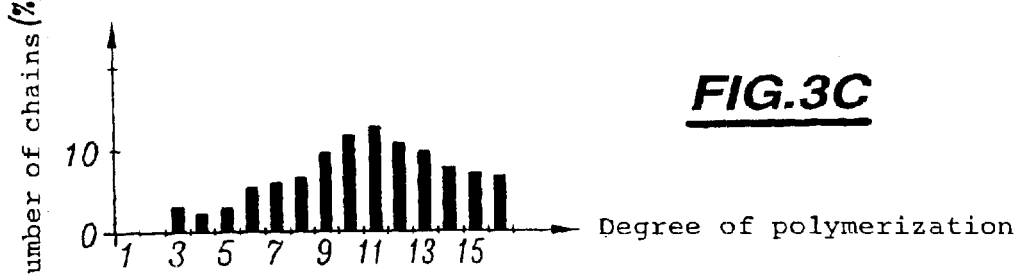
FIG. 3C represents the length distribution for the chains of the debranched amylopectin of the *Chlamydomonas reinhardtii* mutant strain JV45J.

APTS (8-aminopyrene-1,3,6-sulphonic acid) labelling was carried out on the reducing ends, before separating the chains as a function of their length on sequencing gel. Although no change is detected in the length distribution for chains of the amylose, significant modification of the distribution of the very short chain lengths is observed for the amylopectin (FIG. 3C compared to FIG. 3B).

The length distribution for the chains of the amylopectin of the wild-type and mutant strains after debranching with isoamylase was confirmed by capillary electrophoresis of the APTS-labelled glucans according to the method described by O'Shea et al., 1996. Significant modification of the distribution of the very short chains is observed in the mutant JV45J, compared to the wild-type strain. A subtractive analysis, in which the differential percentage of the total mass of each oligosaccharide is obtained by subtraction of the chain length distribution for the debranched amylopectins, confirms the enrichment of the range of extra-short glucans (DP 3, 4, 5 at the expense of DP6 to DP11), found in the mutants. These data confirm the action of the D enzyme in vivo on the structure of the amylopectin.

EXAMPLE 4

Novel Functions of the D Enzyme

1. Detection of the Enzymological Defect in the Mutants and Action of the D Enzyme on the Polysaccharides.

The detection of the defect was carried out according to a zymogram technique under denaturing conditions (Mouille et al., 1996). In addition, a detailed enzymological study was carried out on crude and semipurified extracts, for all known enzymes which can participate in the biosynthesis of starch.

This study involves quantitative and qualitative measurements of enzymatic activities, in parallel to kinetic characterizations and analyses of profiles of elution on Mono-Q anion exchange columns (FPLC chromatography). The enzymes tested are as follows: ADP-glucose pyrophosphorylase, phosphoglucomutase, soluble starch synthetase I, soluble starch synthetase II, granule-bound starch synthetase, branching enzymes (two types), debranching enzymes (pullulanase and isoamylase), phosphorylases and all starch hydrolases which can be detected in zymogram gels containing starch. No qualitative or quantitative difference in these enzymatic activities cosegregated with the mutant gene.

During the production of zymograms under denaturing conditions, the absence of a 62 kD band stained dark red with the iodine was observed in the meiosis products carrying the mutation sta11-1 on a zymogram in the presence of starch or of amylopectin, whereas this 62 kD band appears distinctly in the wild-type segregants (n=75). According to the technique developed by Mouille et al., (1996), the polysaccharide from a gel band was eluted and the product was subjected to NMR analysis. The proton spectrum of the amylopectin incubated had been considerably modified. Specifically, the bimodal proton signal, initially from 5.3 to 5.2 ppm, had been replaced with a monomodal signal, at the same position, of 5.2 ppm, under standard NMR conditions.

2. Purification of the Enzyme and Glucan Transfer Activity.

A purification requires 20 liters of culture of a wild-type strain of Chlamydomonas reinhardtii in TAP medium (Harris, 1989) for three days in order to obtain a cell density of 2×10' cells per ml. After centrifugation at 3000 rpm for 10 minutes, the cell pellet is put through a French press twice and immediately frozen at −80° C. This thawed crude extract is centrifuged for 20 minutes at 1000 rpm, at 4° C. The extract proteins (350 to 500 mg) are assayed by the Bradford method (Bio-rad assay kit).

The supernatant is precipitated with 5% protamine sulphate (40 µl per ml of extract, 15 minutes in ice), and then centrifuged at 10 000 rpm for 20 minutes at 4° C.

The supernatant (200 to 400 mg of proteins) is injected, using a multi-injection programme, onto a MonoQ ion exchange column (Pharmacia HR 10/10, with a volume of 9 ml, flow rate: 2 ml.min$^{-1}$) equilibrated in a 50 mM sodium acetate, 2 mM DTT buffer (pH 6 with acetic acid).

The nonretained fraction (40 to 70 mg) undergoes a first precipitation with 30% ammonium sulphate (176 mg/ml) for 45 minutes at 4° C., and is then centrifuged at 1000 rpm for 20 minutes.

The supernatant (30 to 60 mg) is next precipitated to 50% for 45 minutes at 4° C. (126 mg/ml), and is then centrifuged at 10 000 rpm for 20 minutes.

The pellet (10 to 20 mg of proteins) is resuspended in 2 ml of 50 mm sodium acetate, 2 mM DTT buffer, pH 6, and then injected onto S 100 filtration gel (FPLC; Pharmacia sephacryl 2.6×60 cm; flow rate: 2 ml.min$^{-1}$; fraction volume: 2 ml; alkyl dextran support bridged with N,N'-methylene bisacrylamide; spherical gel with a diameter of 25 to 75 µm; fractionation range: 1000 to 10 000) equilibrated in the same buffer. The fractions of interest are collected 30 minutes after the injection, and then detected by revealing the activity on zymograms according to the technique described by Mouille et al., (1996). The enzyme of interest is found in fractions 14 to 26. These fractions are pooled and concentrated using a UnoS12 cation exchange column sold by Bio-Rad (gel with a volume of 15×68 mm, grafted with sulphonic acid groups) in a 50 mM sodium acetate, 2 mM DTT buffer. The disproportionating enzyme is eluted with a continuous NaCl gradient (50 mM sodium acetate, 1 M NaCl buffer) and the enzyme is recovered in the fractions corresponding to the elution with 50% NaCl.

All the column chromatographies are carried out by FPLC on a Pharmacia LCC—S00 apparatus.

Figure 3D:
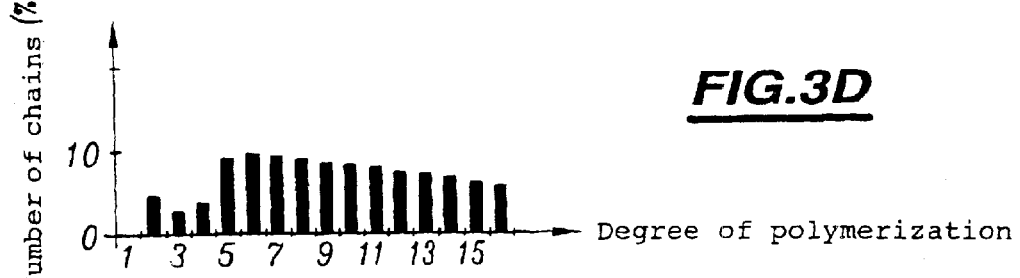
FIG. 3D represents the length distribution for the chains of the debranched amylopectin of "waxy" maize with the pure D enzyme of *Chlamydomonas reinhardtii* in the absence of oligosaccharides.
Figure 3E:
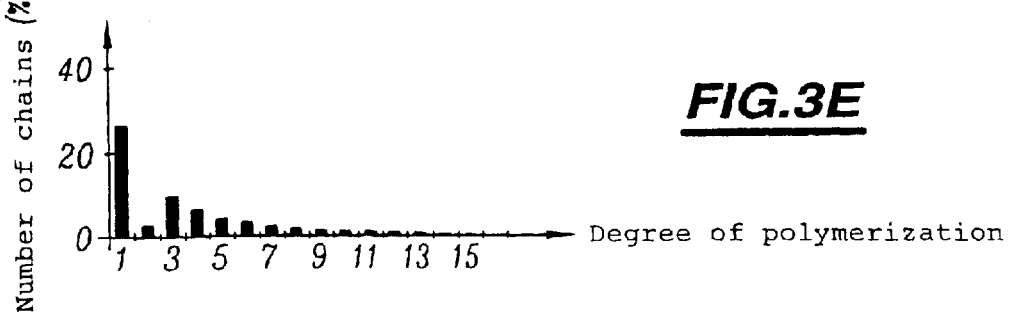
FIG. 3E represents the length distribution for the maltotriose incubated with the pure D enzyme of *Chlamydomonas reinhardtii*.

The pure enzyme reproduced the effects observed on the amylopectin by proton NMR. The incubation of amylopectin with the pure enzyme led to considerable changes in the distribution for the long chains of the amylopectin (FIG. 3D). The action on the amylopectin could be detailed by debranching the incubated product before and after treatment with β-amylase.

As β-amylases are processing enzymes which selectively digest the exterior chains of polysaccharides, the result obtained shows that the major modifications are restricted to the external chains of the polymer. It is important to note that no oligosaccharide is released in the process, while the amount of α-1,6 linkages remains constant. The 62 kD enzyme is, therefore, an α-1,4 glucanotransferase, the function of which is to cleave the α-1,4 linkages present on the external chains of the amylopectin donor in order to transfer them to the nonreducing ends of neighbouring exterior chains of the acceptor. In plants, the only α-1,4 glucanotransferases known to be present in the synthesis of starch are commonly named D enzymes. They are known to act on soluble oligosaccharides at least three glucose residues long (maltotriose) so as to give oligosaccharides of varying length at the expense of the formation of glucose. The reaction consists of cleavage of a donor glucan and transfer to a receptor chain.

The action of the 62 kD enzyme identified was tested, in parallel, on glucose, maltose, maltotriose, maltotetraose, maltopentaose, maltohexaose and maltoheptaose: the enzyme disproportionates with success all the oligosaccharides longer than maltose and glucose, on which it has no action. Its effects on maltotriose have been described in FIG. 3E. The very low amounts of maltose in all these cases confirm that the enzyme obeys the rules presented above defining the action of disproportionating enzymes.

The protocol for purifying the D enzyme can be modified, for example according to the following variant:

The supernatant obtained after centrifugation of the crude extract as described in Example 3 is precipitated with protamine sulphate (50 µl of 10% protamine sulphate per ml of extract, 15 minutes in ice), and then centrifuged at 10 000 rpm for 20 minutes at 4° C.

The supernatant (200 to 400 mg of proteins) is then injected, using a multi-injection programme, onto a MonoQ anion exchange column (Pharmacia HR10/10 with a volume of 9 ml, flow rate: 2 ml.min$^{-1}$) coupled to a UNO—S12 cation exchange column (BIO-RAD, with a volume of 12 ml, flow rate: 2 ml.min$^{-1}$). These two columns are equilibrated in a 50 mM sodium acetate, 2 mM DTT buffer (pH 6 with acetic acid). The elution is carried out with a 30 min step at 5% NaCl. The fractions of interest are collected and then detected by revealing the activity on starch zymograms.

300 µl of sample are loaded onto a maltotriose affinity column (SIGMA: maltotriose immobilized on agarose. Volume: 1 ml) equilibrated in a 50 mM sodium acetate, 2 mM DTT buffer (pH 6 with acetic acid). The column is washed with 2 ml of this same buffer and the elution is carried out with a 50 mM sodium acetate, 1 M NaCl buffer.

|  | Total activity nmol/min | specific activity nmol/min/mg |
|---|---|---|
| before affinity column | 92.1 | 2046 |
| after affinity column | 13.95 | 93 000 |
|  | Yield | Purification factor |
|  | 15% | 45% |

The activity thus purified occurs at an optimum pH of between pH 5 and pH 7.5, and decreases significantly above pH 9.

3. Incorporation of Olicosaccharides onto the External Chains of Glycogen

The incorporation of labelled maltooligosaccharides onto glycogen provides a further example of the activity of the D enzyme demonstrated on the amylopectin, with the zymogram procedure. The co-elution of the 62 kD band (D enzyme) shows an enzymatic activity found in the zymogram procedures and quantitative tests for purifying the enzyme. A cosegregation between the presence of the 3 activities (production of glucose from maltotriose, modification of amylopectin and incorporation of debranched glucans into glycogen) and the wild-type STA11 allele in the individuals derived from the crosses between the wild-type and mutant strains of Chlamydomonas was also demonstrated.

For demonstrating the incorporation of labelled maltooligosaccharides of controlled length (DP1: glucose to DP7: maltoheptaose), the zymogram procedure described in Example 3 was followed: 100 and 300 µg of crude protein extracts were loaded onto gels containing glycogen, and left to incubate separately with 2 mM DP1 (glucose) to DP7 (maltoheptaose), or without maltooligosaccharides (negative control), overnight at room temperature. The appearance of a 62 kD band with the growing length of the donor substrate shows that the effectiveness of transfer to the external chains of glycogen increases with the length of the donor chain. No labelling is observed when maltotriose is used as a donor substrate, even at very high substrate concentration (20 mM) and after sustained incubation (48 h). Glucans which are longer than maltotetraose therefore define the current substrate preferred for the incorporation reaction. They are thought to be produced in vivo during the maturation of pre-amylopectin by isoamylases.

The zymogram system mimics the synthesis of polysaccharide at the surface of the starch granule quite well in that it allows the oligosaccharides to diffuse freely in a large volume of buffer, whereas the polysaccharide is retained in a small volume of the gel, which is where high specific enzymatic activity occurs.

4. Novel Polymerase Function of the D Enzyme.

Oligosaccharides are radioactively labelled with $^{14}$C by in vivo debranching of the labelled amylopectin. It was verified that the length distribution for the chains in the mixture of the debranched chains corresponded to that shown in FIG. 3B.

Figure 4:
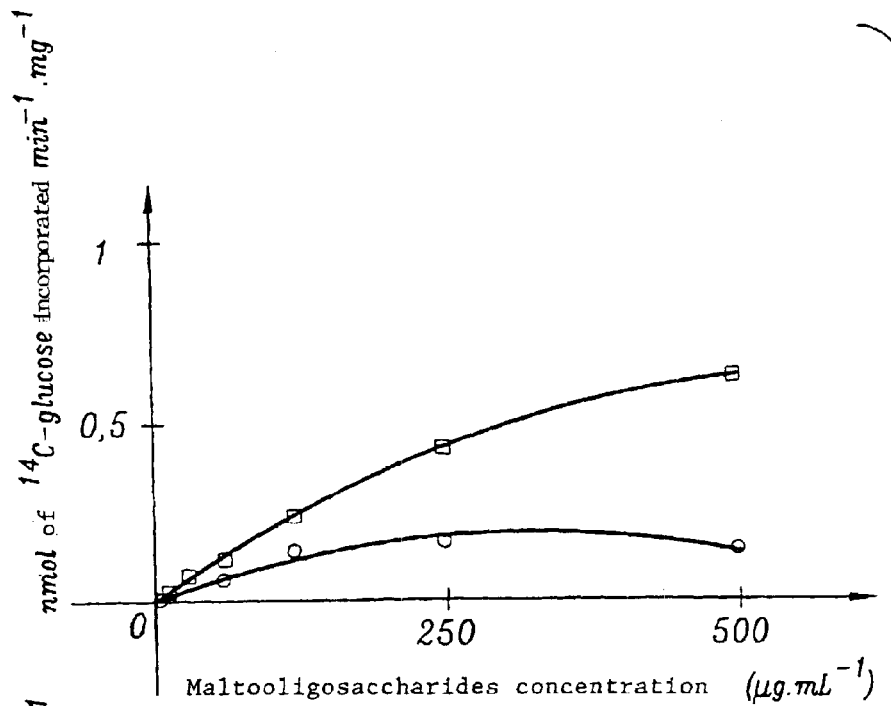
FIG. 4 represents the incorporation of maltooligosaccharides onto the amylopectin of the wild-type strain of *Chlamydomonas reinhardtii*.
Figure 4:
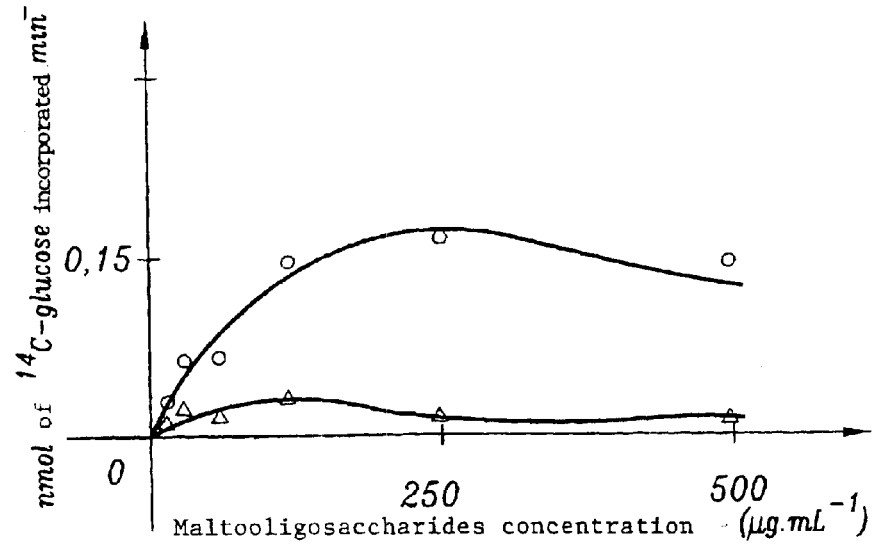

The incorporation of the oligosaccharides into the amylopectin (FIG. 4) or the glycogen of rabbit liver was successfully measured, at physiological concentrations of maltooligosaccharides. Specifically, the D enzyme showed very effective polymerase activity on the glycogen and on the amylopectin. The substrates and products of the reaction were separated by molecular sieve chromatography in TSK-HW-50 gel (glyogen) or in CL2B sepharose.

The incorporation of the labelling of the maltooligosaccharides onto the amylopectin provides a more reliable assay on the activity of the D enzyme, compared to the production of glucose.

It was, moreover, demonstrated that the polymerization in vitro was located on the external chains of the amylopectin. Specifically, the signal of radioactivity incorporated into the polysaccharide disappears when the amylopectin which has undergone the incorporation of the oligosaccharides is placed in the presence of β-amylase, this being an enzyme specific for the external chains of the amylopectin.

EXAMPLE 5

Production of Transgenic Maize Plants

A. Production and Use of a Maize Callus as a Target for Genetic Transformation.

The genetic transformation of maize, whatever the method employed (electroporation, biolistics, microfibres, particle gun), generally requires the use of rapidly dividing undifferentiated cells which have conserved an ability to regenerate whole plants. This type of cell composes the embryogenic friable callus (termed type II) of 4 maize.

These calluses are obtained from immature embryos of genotype H1 II or (A188×B73), according to the method and on the media described by Armstrong (1994). The calluses thus obtained are multiplied and maintained by successive subculturings every fortnight on the initiation medium.

Plantlets are then regenerated from these calluses by modifying the hormonal and osmotic balance of the cells according to the method described by Vain et al (1989). These plants are then acclimatized in a greenhouse, where they can be crossed or selfpollinated.

B. Use of the Particle Gun for the Genetic Transformation of Maize.

The preceding paragraph describes the production and regeneration of the transformation cell lines. Described here is a method for genetic transformation which leads to the stable integration of the modified genes into the genome of the plant. This method is based on the use of a particle gun. The target cells are fragments of calluses described in paragraph A. Four hours before bombardment, these fragments, with a surface area of 10 to 20 mm$^2$, were placed, in a proportion of 16 fragments per dish, at the centre of a Petri dish containing a culture medium identical to the initiation medium, supplemented with 0.2 M of mannitol+ 0.2 M of sorbitol. The plasmids carrying the nucleotide sequences to be introduced, such as the cDNA encoding the D enzyme of potato (Takada et al., 1993) or the antisense sequences obtained from this cDNA, are purified on a Qiagen column, following the manufacturer's instructions. They are then precipitated on particles of tungsten (M10) according to the protocol described by Klein et al (1987). The particles thus coated are projected towards the target cells using the gun and according to the protocol described by J. Finner (1992).

The dishes of calluses thus bombarded are then sealed using ®Scellotrais, and then cultured in the dark at 27° C. The first subculturing takes place 24 hours later, and then every fortnight for three months on medium identical to the initiation medium supplemented with a selective agent. The selective agents which can be used consist generally of active compounds of certain herbicides ®Basta, ®Roundup) or certain antibiotics (hygromycin, kanamycin, etc.).

After three months, or sometimes earlier, calluses are obtained in which the growth is not inhibited by the selection agent, and which are usually and mainly composed of cells resulting from the division of one cell which has integrated into its genetic inheritance one or more copies of the selection gene. The frequency of production of such calluses is approximately 0.8 calluses per dish bombarded.

These calluses are identified, separated, amplified and then cultured so as to regenerate plantlets. In order to avoid any interference with nontransformed cells, all these operations are carried out on culture media containing the selective agent.

The plants thus regenerated are acclimatized and then cultured in a greenhouse, where they can be crossed or selfpollinated.

C. Use of *Acrobacterium tumefaciens* for the Genetic Transformation of Maize.

The technique used is described by Ishida et al., 1996.

EXAMPLE 6

Demonstration of the Role of the D Enzyme in the Degradation of Maltooligosaccharides by Phosphorylase It is suggested that, in the bacterium, amylomaltase, an α-1,4 glucanotransferase similar to the D enzyme, increases the production of glucose-1-phosphate by maltodextrin phosphorylase, by generating glucans which are long enough (DP5) to be usable by the phosphorylase (Boos et al., 1998). Measurement of the production of glucose-1-phosphate from maltotriose, maltotetraose, maltopentaose and maltoheptaose (2.5 mM), in the presence of 100 μg of extracts of the wild-type (137° C.) and mutant sta11-1 (JV45J) strain of Chlamydomonas, demonstrated an at least 5-fold stimulation, in the presence of D enzyme, of the degradation of the maltotetraose and of the maltotriose by the phosphorylase. Since it is known that the production of glucose-1-phosphate from glucan of length DP5 is found both in bacteria and plants, the D enzyme might also facilitate the action of the phosphorylase in plants.

EXAMPLE 7

Cloning of the Sequences Encoding the D Enzyme

A preliminary gene assay analysis in deploid and triploid, wild-type and mutant respectively, strains made it possible to establish a correlation between the number of wild-type STA11 alleles and the amount of corresponding enzyme.

The isolation of genomic sequences encoding the D enzyme of Chlamydomonas was carried out according to the following protocol: sequence alignment carried out between *Solanum tuberosum, Streptococcus pneumoniae, Mycobacterium tuberculosis* and *Clostridium butyricum* made it possible to choose oligonucleotides corresponding to the conserved regions (regions 1 and 2), to be used as primers for PCR reactions. In order to facilitate the cloning of a possible PCR fragment, a 16-nucleotide extension containing the restriction sequences of 3 different enzymes was added in

| Region 1 | Region 2 |
|---|---|
| P.G.P.Y.G.I.G | R.I.D.H.F.R.G.F |
| Corresponding degenerated oligonucleotide | Corresponding degenerated oligonucleotide |
| 5'[AGAATTCCGCGGCCGC]CCNGGYSCSTAYGGYATYGG3' | 5'(AGAATTCCGCGGCCGC]RAARCCVGCRAAATGRTCRATVCG3' |

All the PCR reactions were carried out with the taq DNA polymerase from GibcoBRL Life Technologies, which is coupled to an antibody and becomes active only after a 3 minute passage at 94° C.

The optimum conditions for the specific amplification of the region of interest are as follows: an MgCl, concentration of 3 mM and the following programme sequence:

3 minutes at 94° C.
45 seconds at 94° C.
30 seconds at 62° C.
1 minute 30 seconds at 72° C.
repetition of steps 2 to 4, 35 times
10 minutes at 72° C.
conservation at 40° C.

A band of approximately 1.6 Kb could thus be amplified from genomic DNA.

This PCR product is extracted from a 0.8% TAE gel according to the "DNA Purification Kit" protocol from PROLABO, and placed into the multiple cloning site of the plasmid pbluescript II SK at the NotI site. Transformation of the strain XL1-Blue of *Escherichia coli* made competent then allows the amplification of the clone. Rapid sequencing of the 1.6 Kb (between the T3 and T7 primers) was then carried out according to the Sanger method (SEQ ID No. 1).

The cloning, in the mutant sta11-1, of the region corresponding to the gene of the D enzyme can be carried out, according to a suitable protocol, in order to determine the nature of the mutation which leads to the absence of the protein in the mutant cell. The demonstration of allele modification specific to the restriction profile of the mutated strain, and the study of the cosegregation of the restriction polymorphism and of the mutation in the segregants of a cross between a wild-type strain and an STA11 strain may make it possible to correlate definitively the STA11 gene with the D enzyme.

EXAMPLE 8

Conditional Expression of the Mutation

A comparative analysis of the wild-type and mutant sta11-1 strains, under conditions lacking nitrogen or under normal conditions, shows that the expression of the mutant sta11-1 phenotype is partially conditional. This indicates that the expressiveness of the mutation on the phenotype can vary as a function of the physiological conditions, for the same organism. It is possible that these variations in expressiveness of the phenotype are found from one plant species to another. It is possible to find conditions under which the drop in the amount of starch does not occur, even though phenotypic modifications are observed (presence of oligosaccharides, modification of the structure of the amylopectin).

The table below gives the results obtained on the phenotypes of the wild-type and mutant strains in the synthesis of transition or storage starch, respectively, using a culture not lacking nitrogen (+N) and a culture lacking nitrogen (-N).

Phenotype of the Wild-Type and Mutant Strains in the Synthesis of Transition or Storage Starch:

The values listed are the mean of three separate measurements in a single experiment.

| Strain | Genotype | Ap λmax[a] | | Starch[b] | | MOS[c] | | Am %[d] | |
|---|---|---|---|---|---|---|---|---|---|
| | | +N | -N | +N | -N | +N | -N | +N | -N |
| CO23 | + | 566 | 560 | 1.2 | 13 | 0.011 | 0.018 | 1 | 14 |
| CO65 | + | 570 | 542 | 0.4 | 24.7 | 0.007 | 0.001 | 2 | 15 |
| CO35 | + | 564 | 554 | 0.91 | 22.8 | 0.012 | 0.017 | 5 | 25 |
| CO29 | sta11-1 | 576 | 570 | 1 | 1.7 | 0.45 | 0.45 | 7 | 38 |
| CO137 | sta11-1 | 572 | 564 | 2 | 0.83 | 0.3 | 0.17 | 10 | 25 |
| CO214 | sta11-1 | 575 | 562 | 0.31 | 0.78 | 0.2 | 0.2 | 12 | 24 |

[a]Ap λmax, wavelength of the maximum absorbance of an iodinated polysaccharide complex of amylopectin purified by gel filtration.
[b]amount of insoluble polysaccharide, expressed in μg · $10^{-6}$ cells, purified by sedimentation (measurement by standard assay of the amyloglucosidase).
[c]MOS: amount of soluble maltooligosaccharides, expressed in μg · $10^{-6}$ cells. 0.5 μg · $10^{-6}$ cells corresponds to a plastidial concentration of 10 mM if all the MOS was to be considered as being maltotriose.
[d]The percentage of amylose in the purified starch was calculated by gel filtration of the dispersed polysaccharides.

BIBLIOGRAPHY

An G. (1986), Plant Physiol. 81: 86–91
Armstrong et al., (19.94), Maize handbook; M. Freeling, V. walbot Eds, 665–671
Bensen et al., January 1995, The Plant Cell, Vol. 7, 75–84
Buleon et al., (1997), Plant Physiol., 115: 949–957
Das et al., March 1995, The Plant Cell, Vol. 7, 287–294
Delrue et al., (1992), J. Bacteriol., 174, 3612–3620
Depicker et al., (1982) J. Mol. Appl. Genet., 1, 561–573
Finner J. et al., (1992), Plant Cell Reports, 11, 323–328
Franck et al., (1980) Cell. 21, 285–294
Fromm M. E., Taylor L. P., Walbot V., (1986) Nature, vol. 319, 791–793
Gaubier et al., Mol. Gen., 238, 409–418 (1993)
Ishida et al., (1996), Nature biotechnology, 14, 745–750
Jouanin, Plant. Sci., 53, 53–63 (1987)
Harris et al. (1989) San Diego: Academic Press, 25–63
Haseloff et al., Nature 334, 585–591, 1988
Kay, Science, (1987) 236, 1299–1302
Klein et al., (1987), Nature, 327, 70–73
McElroy (1991) Mol. Gen. Genet. 231: 150–160
McClintock, B. 1950, Proc. Natl. Acad. Sci. USA 36, 344–355
Mouille et al., (1996), Plant Cell 8, 1353–1366
Ni et al., Pint J., (1995) 7, 661–676
O'Shea et al. (1996), electrophoresis 17, 681–688
Sanford J. C., (1988) Trends in Biotechnology, 6, 299–302
Takaha et al., 1993, J. Biol. Chem. vol. 268, No. 2, 1391–1396
Takada et al., 1998, Planta, vol. 205, No. 3, 445–451
Vain et al., (1989), Plant Cell Tissue and Organ Culture, 18, 143–151
Watson et al., ADN recombinant, (recombinant DNA Ed. De Boeck University, p 273–292
Whistler et al., (1967), Starch: chemistry and technology II—industrial aspects, Academic press, 432–458.

What is claimed is:

1. An isolated nucleic acid comprising a nucleotide sequence selected of sequence SEQ ID No: 1 encoding a protein having α-1,4 glucanotransferase enzymatic activity.

2. An isolated nucleic acid comprising a sequence which is complementary to the sequence according to claim 1.

3. A cloning and/or expression vector comprising the nucleotide sequence according to claim 1.

4. A cloning and/or expression vector comprising the nucleotide sequence according to claim 2.

5. A method for modifying a starch produced by a plant, said starch comprising an amylopectin that is enriched in chains containing at least 9 glucose residues, with respect to a starch produced naturally by the plants, wherein said method comprises the steps of:

a) constructing an expression vector according to claim 3;
   b) transforming a plant cell with said expression vector; and
   c) regenerating the plant from the cell transformed in step b, said transgenic plant thus obtained producing a starch comprising an amylopectin that is enriched in chains containing at least 9 glucose residues.

6. A plant, or part of a plant, comprising the cloning and/or expression vector of claim 3 in which the level of expression of an α-1,4 glucanotransferase enzyme encoded by the nucleotide sequence as of SEQ ID NO:1 is increased in the cells of said plant so that said plant produces a modified starch comprising an amylopectin that is enriched in chains containing at least 9 glucose residues, with respect to a starch produced naturally by the plant.

7. The plant or part of a plant according to claim 6, wherein said plant is selected from the group consisting of potato, wheat, maize and rice.

* * * * *

SEQUENCE LISTING

<160> NUMBER OF SEQ ID NOS: 1

<210> SEQ ID NO 1
<211> LENGTH: 1557
<212> TYPE: DNA
<213> ORGANISM: Chlamydomonas reinhardtii

<400> SEQUENCE: 1

```
ccgggtgcgt acggtattgg cgatattggt gatgaggcca agcgcttcgt cgactggctc      60
gccgaccacg gcatgcagtg ctggcagctg ctgccgctgg tgccccccgga ccccatgtac     120
tactcccct actcgggcac ggacgccaac tgcggcaacc cccttgtggt gagcattgag       180
gagctcatca aggacggact gctggagttc tcggagacgc ccccgcgcgt gcccatcgcc      240
gacgttgact atcccgctgt ggccgcggcc aagctgcccc tgctcaagcg cgcggcgcag      300
cggctgctta aggaggaccg cttcacgcgg ctgcgggagg aatacctcaa gtaccgcaaa      360
gagcacccct gggtggagta cagcgcgctg tttgatgtgg cgcgcaacct gccggagctg      420
agccagttgg cgtggtggca gtggccgagc cgttgcgctg cgcagaagga ggcgctcaag      480
gagttccggg agacaaacaa ggacgcaatt gacgagttcg ttgtgatcca gtacttcttc      540
gagaacagtg gaaggcgatc cgggtgggtt acggctgggg gtgagggtta ccgggagggt      600
ttggacgcca ggcttacggt gtccagccgg cccgccccgt tggcggcggg gaaacggcat      660
gcagggtggg ggcgtttgtg catggcctgg tgccacggac gtatggcgct gacatcacat      720
gccgtgtgtc gggtagcgtc tgcacgcagc gagctggtgc tctgtgccta tcagcacacc      780
gaccccacg ccctcgctca cactggtccg tggccatgtg ccctgaccct gtcacatccg       840
tccttgcttt tgcactgctg cagtcctacg cgaacggcaa gggcatcaaa ctcatcggcg      900
acatgccatc tacgtgggcg gccacagcgc agatgtgtgg ccaaccgcca cctgttcgag      960
ctgaacgagg cggcctgccc gagcaggtca gcggagtgcc gccggacgcc ttctcagcaa     1020
cgggtgaggc cggcgctacg gtggtgcggt gcggtgcggt gtaagagtgc agggcgagcc     1080
tgcacggaat ggggcatagc tgtgcgctgg agagttgggg cgaggcgacg attgggcatg     1140
gtggtggtgg acacaggcgt ccggtatccg gagttacgag ggagcaaggg aaagggtcg      1200
acaccgtgcg tgcaggacgc gcaagcaagc cgtgcgccgc tatctgtatt acctggcgtt     1260
accgtgcgta tgtgcgtagc gcggcaggat ggatgaagca aggggctgg cggcgctcag      1320
```

```
gcagccagta ggaatatgag cggggtgggg cccacggtag catacctcct taacataacg    1380
gttcgccctg ggactgaatc gccgcgcctg ctgccgtcac caacaggcca gctgtggggc    1440
agcccgcttt acaagtggcc ggcccacaag aaggagggct tcaagtggtg gacggcgcgc    1500
atggcccgga ccctggagct gtacgacgag tgccggatcg accatttcgc cggtttc      1557
```